United States Patent
Brown

(10) Patent No.: US 8,358,738 B2
(45) Date of Patent: Jan. 22, 2013

(54) RESPIRATION-CORRELATED RADIOTHERAPY

(75) Inventor: Kevin Brown, Horsham (GB)

(73) Assignee: Elekta AB (Publ) (SE)

( * ) Notice: Subject to any disclaimer, the term of this patent is extended or adjusted under 35 U.S.C. 154(b) by 258 days.

(21) Appl. No.: 12/870,256

(22) Filed: Aug. 27, 2010

(65) Prior Publication Data
US 2012/0051515 A1    Mar. 1, 2012

(51) Int. Cl.
*A61N 5/10* (2006.01)
(52) U.S. Cl. .................................. 378/65; 378/8; 378/95
(58) Field of Classification Search ................ 378/8, 65, 378/95
See application file for complete search history.

(56) References Cited

U.S. PATENT DOCUMENTS

| 7,356,112 | B2 | 4/2008 | Brown et al. |
| 7,570,738 | B2 * | 8/2009 | Khamene et al. ............... 378/65 |
| 2008/0031404 | A1 | 2/2008 | Khamene et al. |

FOREIGN PATENT DOCUMENTS

| WO | 2008/040379 A1 | 4/2008 |
| WO | 2010/066265 A1 | 6/2010 |

\* cited by examiner

*Primary Examiner* — Jurie Yun
(74) *Attorney, Agent, or Firm* — Westman, Champlin & Kelly, P.A.; Z. Peter Sawicki

(57) ABSTRACT

An approach to radiotherapy is disclosed which allows the therapeutic beam to be more accurately directed towards a target region. Instead of stopping acquiring images during treatment, the system continues to acquire images as treatment is ongoing. This ongoing pipeline of images is used to update the previously created 3D reconstructions of each breathing phase. Thus the position of the target region can also be updated. The surrogate is recorded simultaneously with the image acquisition although it is not used to determine the breathing phase. As new images are used to update the 3D reconstructions of each breathing phase the values of the surrogate associated with that phase are also updated. This means that the correlation with the surrogate can also continue to be evaluated, and the correlation refined, thus improving the ability of the system to track the motion of the target.

12 Claims, 6 Drawing Sheets

RESPIRATION-CORRELATED RADIOTHERAPY

FIELD OF THE INVENTION

The present invention relates to improvements in respiration-correlated radiotherapy.

BACKGROUND ART

Radiotherapeutic apparatus and techniques have now developed to the point where it is likely that some form of tracking or gating system to reduce the effects of tumor motion (primarily due to breathing) will soon be feasible. Such techniques offer significant advantages in terms of the treatment of tumors in the chest and lung area. They require, however, a source of information as to the current location of the tumor, during treatment, in real time. Full 3-D imaging of the tumor requires significant computing time, which introduces an unacceptable lag between the image acquisition and the treatment.

Most existing respiration correlation systems use some form of surrogate monitoring system which has a fast response time, in conjunction with a correlation to the internal tumor position. In other words, rather than try to achieve the difficult task of monitoring the actual position of the tumor, either a feature in the patient is identified, or a marker is provided, whose position can more easily be tracked and is correlated with that of the tumor.

One such method is disclosed in our earlier PCT application WO 2010/066265. In that application, many breathing phases are sampled, and therefore the correlation between the surrogate position and the tumor position is an average with a high statistical confidence. However, once imaging of the patient has stopped, the relationship between the surrogate and the target position is assumed from the earlier measurements. Any change in the surrogate-target relationship over time will cause inaccuracy in the targeting of the therapeutic radiation beam.

Other methods use only a few breathing cycles to determine the correlation between the surrogate and the target region. This enables the correlation to be determined rapidly, and new correlations can be determined during treatment. However, as they are based on a small number of breathing cycles, such methods are susceptible to the sampled breathing cycles not being representative of the ongoing surrogate correlation.

SUMMARY OF THE INVENTION

The present invention provides a method of radiotherapy in which the therapeutic beam may be more accurately directed towards a target region, e.g. a tumor.

Instead of stopping acquiring images during treatment, the system continues to acquire images as treatment is ongoing. This ongoing pipeline of images is used to update the previously created 3D reconstructions of each breathing phase. Thus the position of the target region can also be updated. The surrogate is recorded simultaneously with the image acquisition although it is not used to determine the breathing phase. As new images are used to update the 3D reconstructions of each breathing phase the values of the surrogate associated with that phase are also updated. This means that the correlation with the surrogate can also continue to be evaluated, and the correlation refined, thus improving the ability of the system to track the motion of the target.

In one aspect, therefore, the present invention provides a method of treating a cyclically varying target region in a patient, the method comprising acquiring a first plurality of internal images of the patient, acquiring a signal from the patient, the signal being one capable of acting as a surrogate for the location of the target region in the patient, using the first plurality of internal images, establishing a relationship between the location of the target region and the surrogate signal, beginning treatment of the target region on the basis of the surrogate signal and the established relationship, during said treatment, acquiring a second plurality of internal images of the patient, and updating said relationship on the basis of a dataset including said second plurality of internal images, continuing said treatment on the basis of the surrogate signal and said updated relationship.

The internal images of the patient can be projection images, such as are obtained in the process of cone-beam computed tomography (CBCT). Other imaging modalities can be used, however. Where CBCT is used, the step of establishing a relationship can comprise the substeps of reconstructing a plurality of volumetric images of the patient from the first plurality of projection images, each volumetric image being reconstructed from projection images having a like breathing phase, identifying the position of the target structure in each volumetric image, associating the surrogate signal with the projection images; and determining a relationship between the surrogate signal and the position of the target region. The projection images can be analysed for their breathing phase on the basis of a feature in the images, and those having a like breathing phase can be grouped for reconstruction.

Multiple values of the surrogate signal that are associated with multiple internal images of the first plurality of internal images having a like breathing phase can be used to determine a mean value of the surrogate signal for the target position associated with that phase. The step of updating the relationship then comprises the use of values of the surrogate signal associated with images of said second plurality of internal images having said phase, to update said mean value.

Multiple values of the surrogate signal associated with a like breathing phase can be used to determine a variation of the value of the surrogate signal for the target position associated with that phase.

The treatment will generally comprise directing a radiation beam towards said target region.

In another aspect, the present invention provides a radiotherapy apparatus comprising a patient imaging system for obtaining imaging data of a patient, a sensor for obtaining a surrogate signal indicative of the location of a target region in the patient, a source of penetrating radiation for therapeutic purposes, and control circuitry for directing the source of penetrating radiation towards the target region on the basis of imaging data provided by the patient imaging system, the control circuitry being configured to receive a first set of imaging data, receive surrogate signal values for first set of imaging data, establish a relationship between the location of the target region and the surrogate signal, begin treatment of the target region on the basis of the surrogate signal and the established relationship, during said treatment, receive a second set of imaging data, update said relationship on the basis of a dataset including said second set of imaging data; and continue said treatment on the basis of the surrogate signal and said updated relationship.

The patient imaging system preferably comprises a source of diagnostic x-ray radiation and a detector thereof, and the internal images of the patient will then be a plurality of projection images obtained from the detector. As in the first aspect, however, other imaging modalities are possible.

The control circuitry is preferably further configured to reconstruct a plurality of volumetric images of the patient from the first plurality of projection images, each volumetric image being reconstructed from projection images having a like breathing phase, identify the position of the target structure in each volumetric image, associate the surrogate signal with the projection images; and determine a relationship between the surrogate signal and the position of the target region.

The surrogate signal can be the output of a pressure sensor, an optical monitoring system, or an air flow monitor, or the like.

BRIEF DESCRIPTION OF THE DRAWINGS

An embodiment of the present invention will now be described by way of example, with reference to the accompanying figures in which.

DETAILED DESCRIPTION OF THE EMBODIMENTS

The present invention seeks to establish and maintain an accurate relationship between the target region (e.g. a tumor) and a surrogate signal, such that the location of the target region can be accurately tracked both before and during a single session of radiotherapy treatment.

Figure 6:
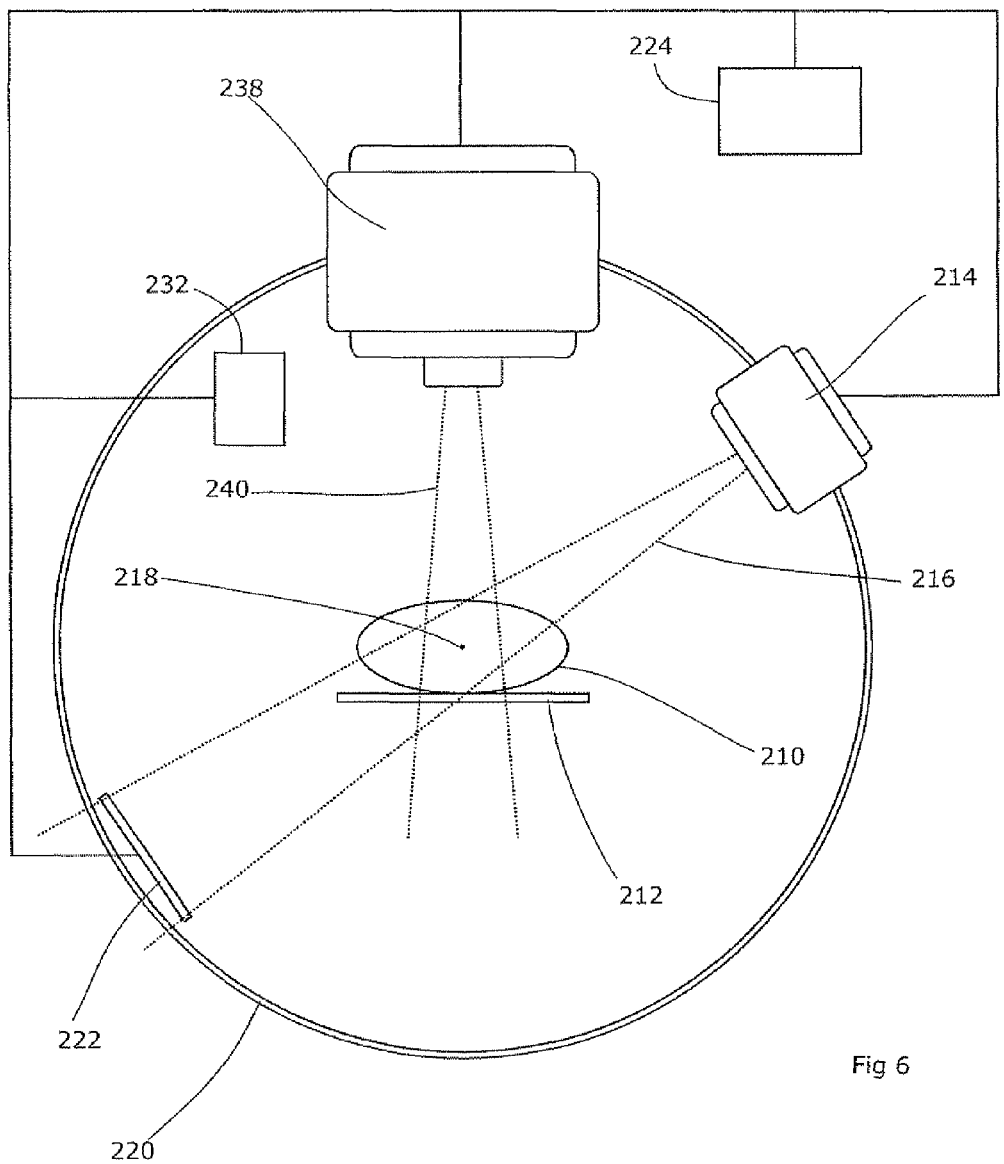
FIG. 6 shows a radiotherapy apparatus according to embodiments of the present invention.

The invention can be performed using a radiotherapeutic apparatus such as is known in the art. FIG. 6 shows one such apparatus.

A patient 210 is supported on a couch 212 which may be of any suitable design. Couches typically allow the elevation and longitudinal position of the patient to be adjusted, and this may be provided for as desired.

An x-ray source 214 is arranged to project a wide beam 216 of radiation generally directed towards the isocentre 218 of the patient. The source 214 is rotatable around the isocentre 218 on a rotational support 220. The support can, for example, be in the form of a ring or annulus around the patient 210 and couch 212 in which the source is mounted, or it can be a C-arm, or any suitable support allowing the source to rotate, or any combination thereof.

A two-dimensional flat-panel detector 222 is also mounted on the support 220, opposite the source 214 and arranged to rotate in synchronism therewith. If the support includes a C-arm then this can be achieved by mounting the detector on the opposite arm.

Thus, radiation emitted by the source 214 is partially absorbed by the patient and the attenuated signal is detected by the flat panel detector 222. The source 214 and detector 222 are then indexed rotationally and a fresh image obtained. This is repeated until sufficient images are acquired to reconstruct the volume data, typically one complete rotation.

The apparatus further comprises cables linking the source 214, detector 222 and rotational support 220 to a plurality of computing means 224 which processes the data generated including the images, source intensity (etc), and rotational support position. Data is output via any suitable means, depicted generally as a monitor 228 but not limited thereto, and the system is controlled by any suitable input means, again depicted generally as a keyboard 230 but likewise not especially limited thereto.

We have found that there are artefacts in the reconstructed volume data of cone beam CT systems, which we have traced to patient breathing movements. To overcome or alleviate these, respiration correlation techniques are applied to the acquired projection images by the computing means 224.

To assist in this process, a surrogate signal acquisition system is provided at 232. Various surrogate signals may be used, and all are within the scope of the present invention. Examples include the Varian RPM system, in which an external marker on the surface of the patient is monitored by a camera, the VisionRT camera-based surface tracking system, the Accuracy system using a marker vest and cameras, and our use of a pressure sensor in the abdominal compression plate (see WO2008/040379). The surrogate signal will usually be one having a low latency, to allow it to be used for gating the radiation beam or tracking the target position.

The apparatus further comprises a therapeutic source of radiation 238 arranged to emit a suitably collimated beam of therapeutic radiation 240. This allows simultaneous scanning and treatment.

Figure 1:
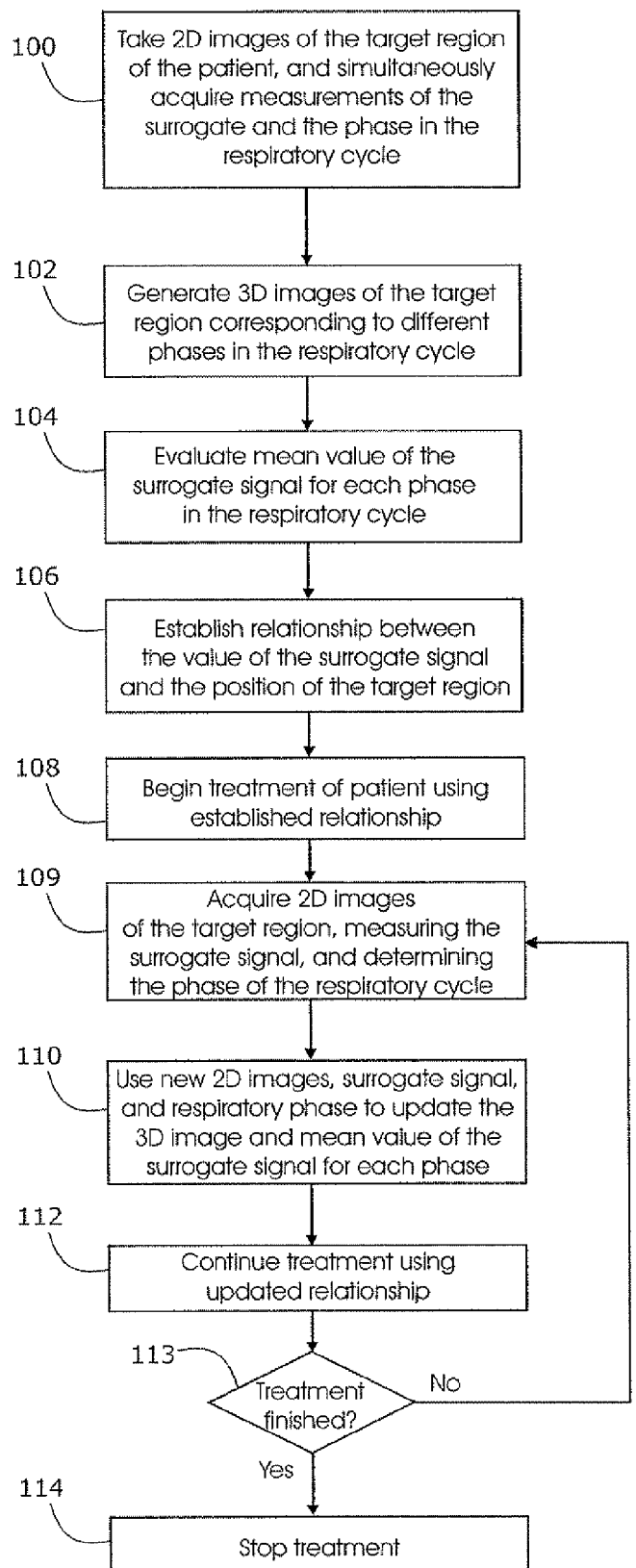
FIG. 1 shows a flowchart of a method according to embodiments of the present invention.

FIG. 1 is a flowchart of a method according to embodiments of the invention.

Figure 2:
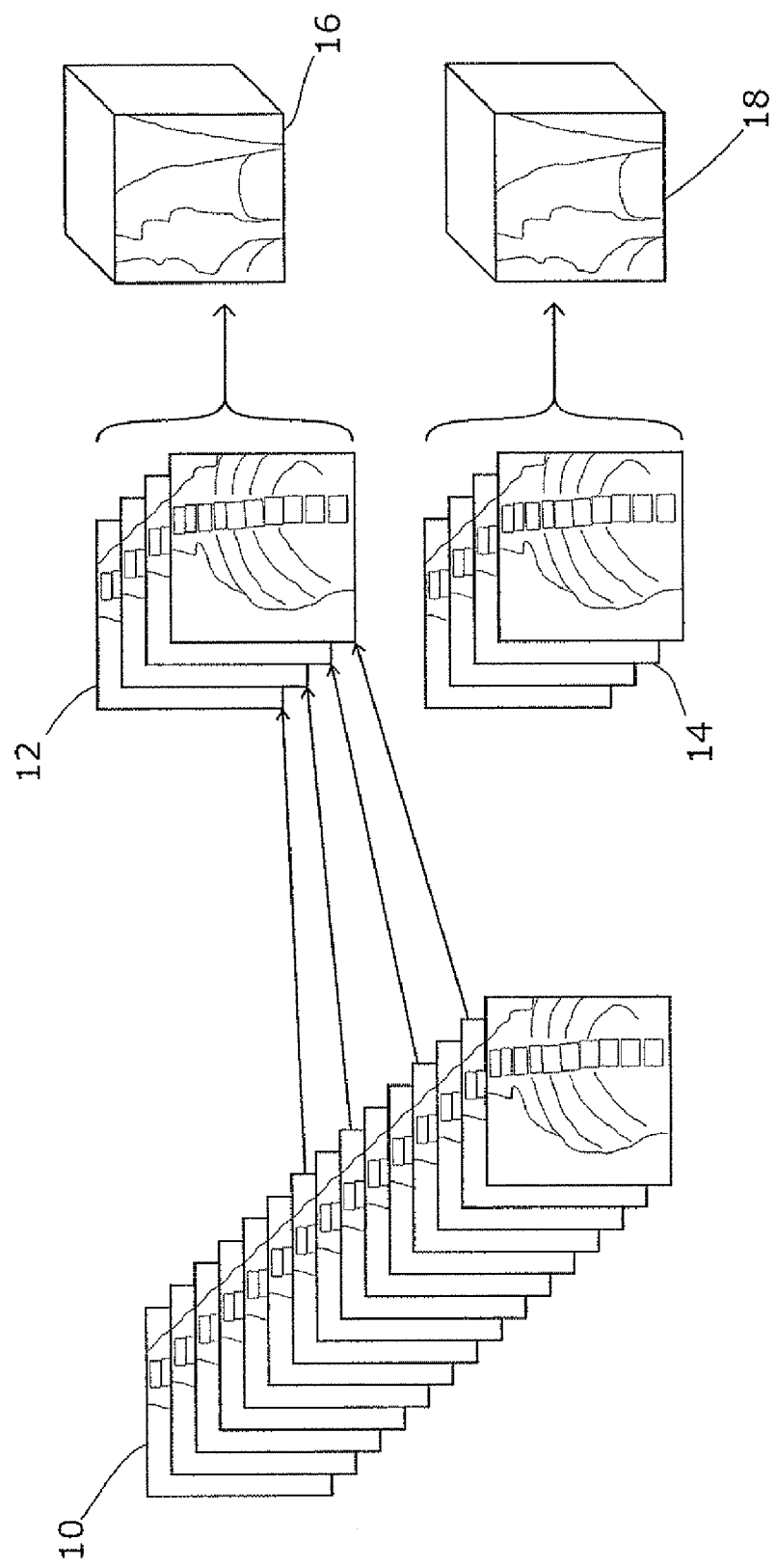
FIG. 2 shows a process for creating a 4D CT dataset.

In step 100, prior to treatment, the patient is placed in the position required for treatment and a CT scan of the region of interest is taken. As shown in FIG. 2, this involves acquiring a series of projection images 10, i.e. a plurality of 2D x-ray images of the region taken from a range of different directions as the imaging head rotates around the patient. Typically, this rotation is about the cranio-caudal axis of the patient.

As each image is acquired, the value of a surrogate signal to be calibrated is recorded and stored in a manner associated with the image. Various surrogate signals may be used, as discussed above.

Each image is then assigned a breathing phase; our preferred way of doing so at present is to analyse the features in the image as set out in our earlier U.S. Pat. No. 7,356,112; that document is therefore incorporated herein by reference and readers are alerted that a reading of that document is essential to a thorough understanding of the present invention. A feature in the image such as the position of the diaphragm provides a suitable indicator of breathing phase. Other features in the image or other methods of determining breathing phase can be employed, however.

Once each image has been allocated a phase, they can be allocated to a suitable group of images 12, 14 consisting of images with like (i.e. similar) phase. Separate three-dimensional CT reconstructions 16, 18 are then obtained from each group 12, 14 (step 102); each CT reconstruction therefore provides a high quality three-dimensional image of the patient structure at a specific point in the breathing cycle.

Figure 3:
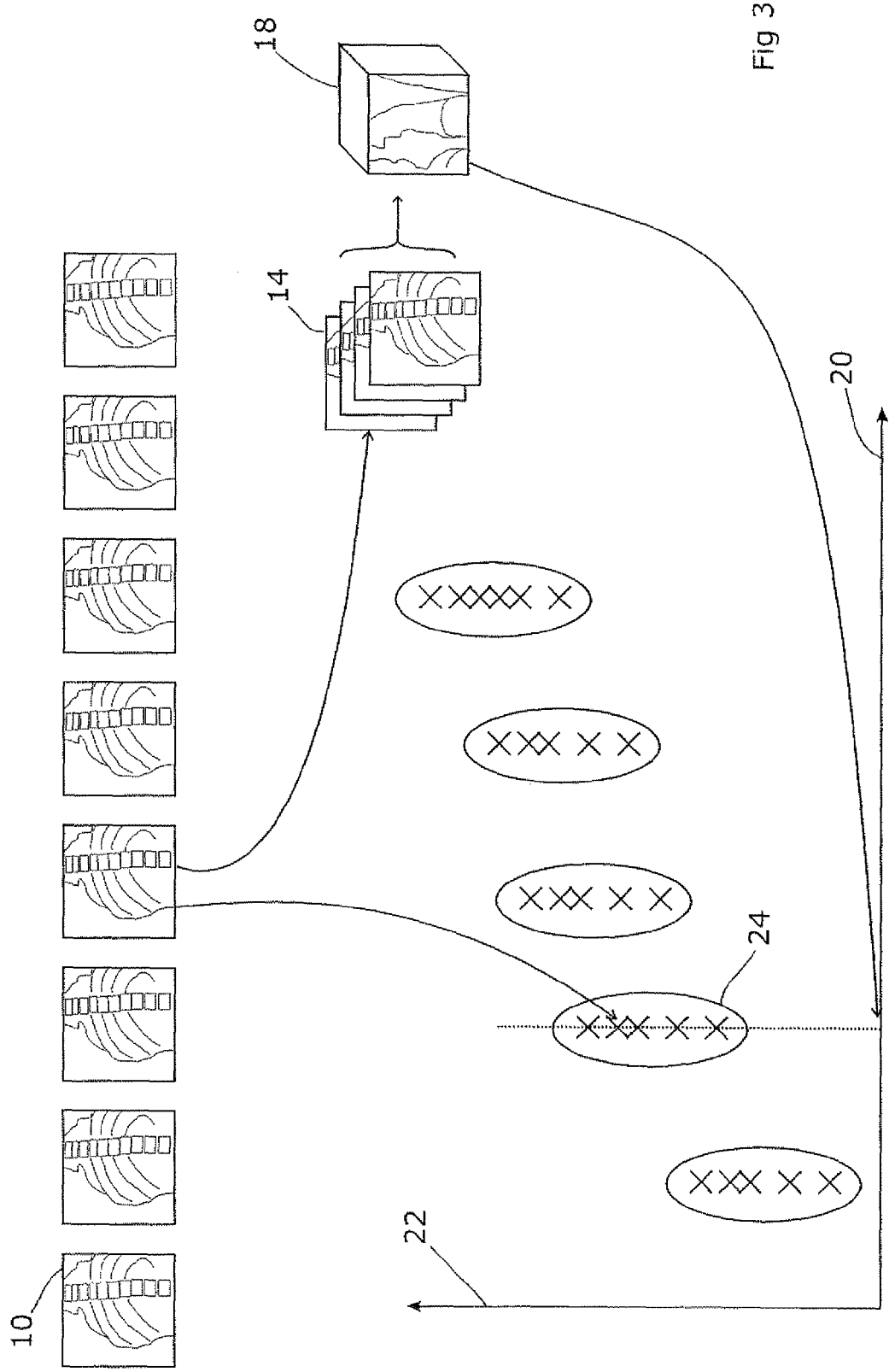
FIG. 3 shows a process for correlation of the surrogate signal and tumor positions.

After reconstruction is completed, the tumor position is determined in each reconstruction, i.e. in each breathing phase. This position can be identified manually by a clinician in each reconstruction, or having identified the position in one reconstruction the position in all other reconstructions can be determined by automated (or semi-automated) analysis of the reconstructions. The value of the surrogate associated with each of the images that contributed to each reconstruction is, of course, already known and recorded. This means that a relationship between the tumor position and the surrogate value can be plotted and analysed. FIG. 3 shows a graph of the relationship, in which the tumor position is plotted along the x axis 20 and the surrogate value plotted along the y axis 22. As can be seen, the process of grouping the images into like breathing phases means that points in the plot (corresponding to images) appear in vertical groups 24, i.e. having nominally the same breathing phase but different surrogate signal values. However, a relationship between surrogate value and breathing phase is clear.

To summarise, the surrogate value associated with each image 10 yields the y position of the plot point corresponding to that image. Images are also grouped according to their breathing phase, and each group 14 is reconstructed to yield a CT dataset 18 from which the tumor position and hence the x position is determined.

Figure 4:
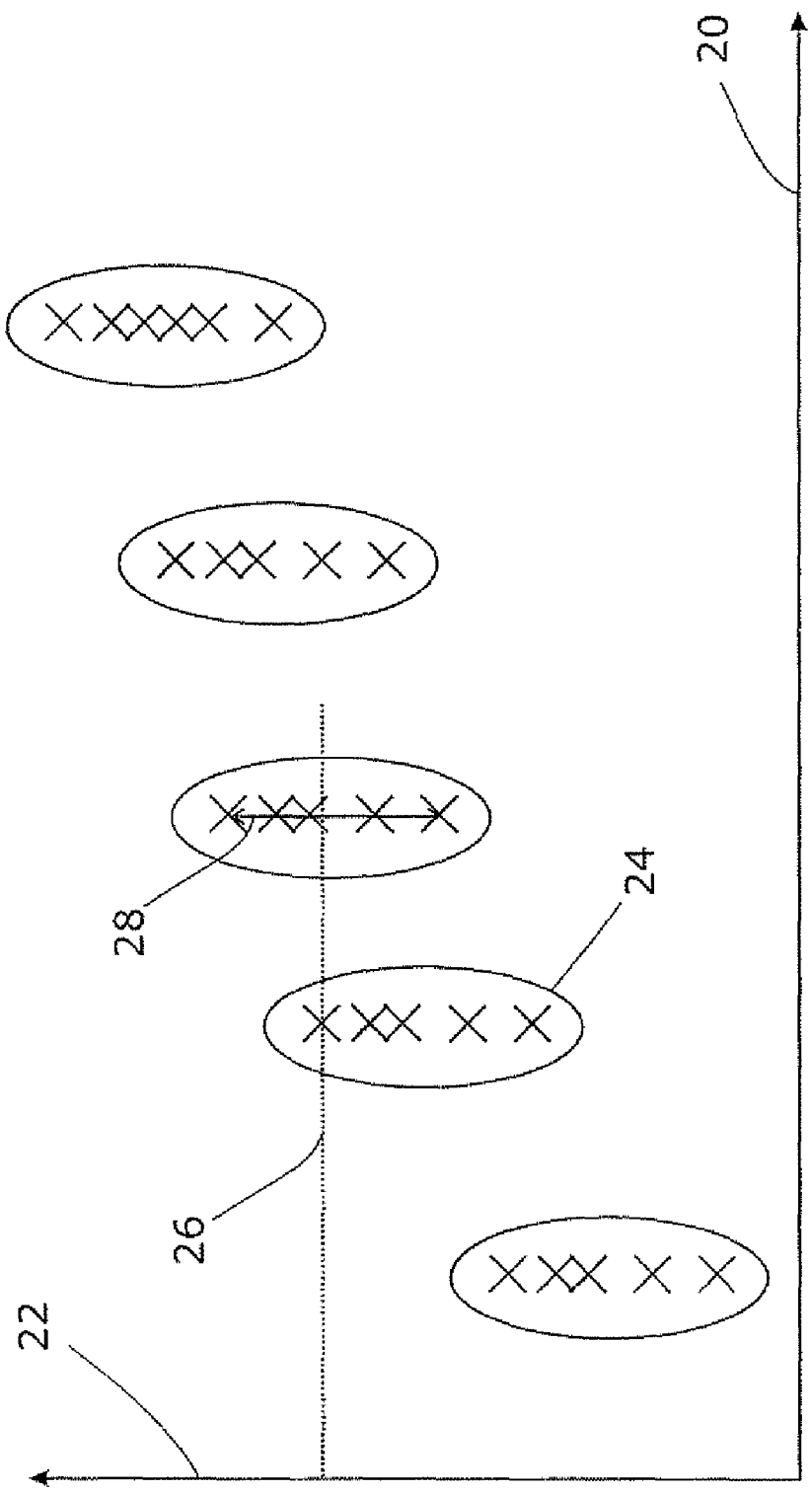
FIGS. 4 and 5 show the derivation of tumor position and confidence data from the correlation.
Figure 5:
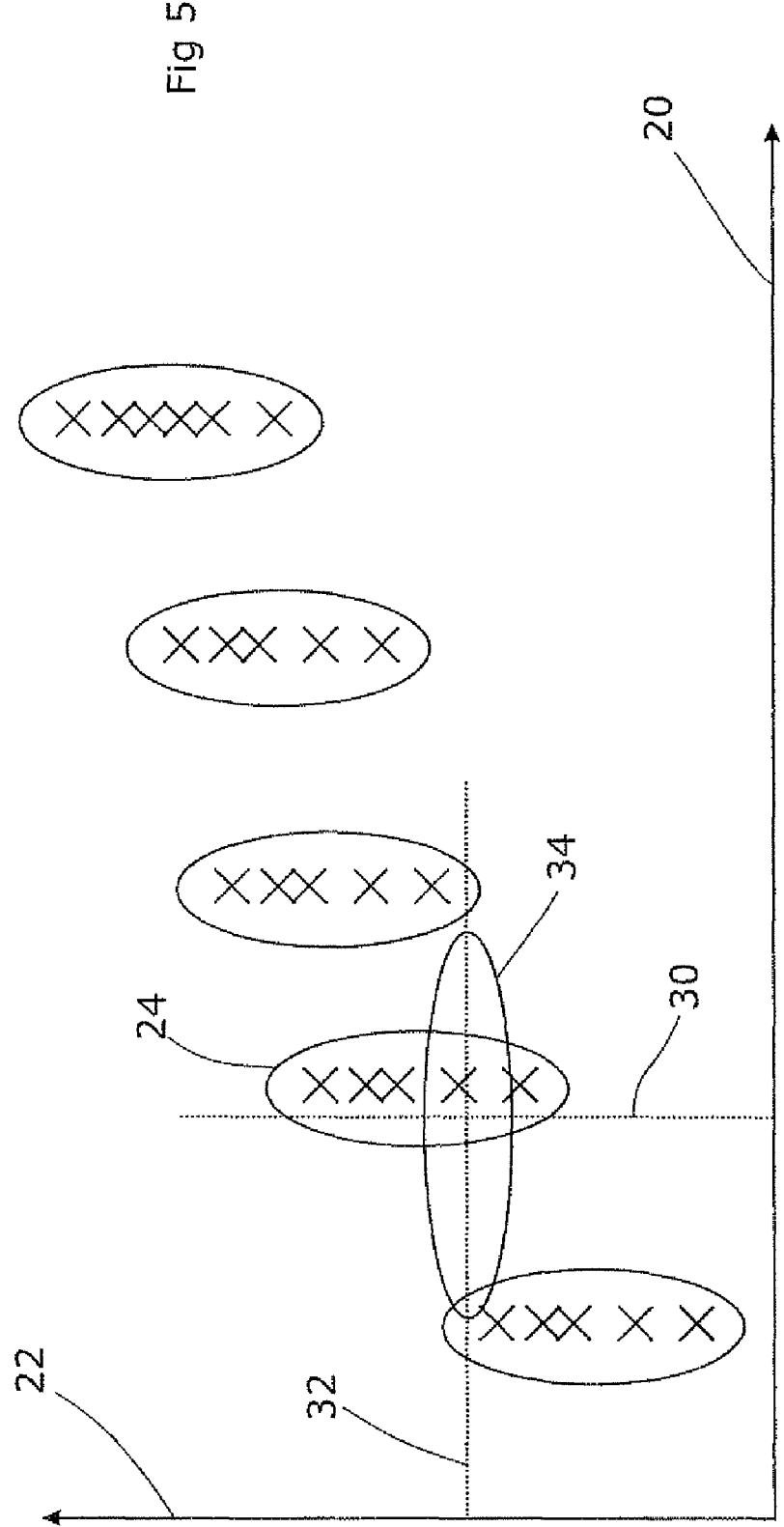

Thus, both the mean value 26 of the surrogate and its variation 28 can be calculated for each breathing phase (step 104), and hence for each of a certain number of tumor positions, as illustrated in FIG. 4. More usefully, as shown in FIG. 5, this data can be used to calculate the most likely position 30 of the tumor for any given value 32 of the surrogate (step 106). This most likely value 30 can be used to drive the tracking or gating system and so direct the therapeutic radiation towards the tumor. Furthermore, as also shown in FIG. 5, the data can be used to derive a confidence value 34 associated with this most likely value 30, and this confidence value 34 indicates the likely residual error associated with the correlation. This can be used to determine the safety margins that are necessary to ensure that the tumor is satisfactorily irradiated.

In step 108, therapeutic radiation is directed towards the tumor using the established relationship between the surrogate signal and the tumor position. That is, the value of the surrogate signal at any one time is translatable into a most likely position of the tumor. The therapeutic radiation can then be directed accurately towards that most likely position. For example, a patient lies on the support while being irradiated by the source. The collimator acts on the radiation beam in a plane transverse thereto, to shape and direct the radiation as appropriate. The gantry rotates about the patient, to allow the radiation beam to access the patient from different directions. In addition, the patient support may move along the translation axis, to allow the radiation beam access to different regions of the patient displaced along the translational direction. The position and orientation of the gantry, patient support and collimator can all be adapted to direct the radiation towards the tumor.

In parallel with this treatment, in step 109, the radiotherapy system continues to acquire images of the target region, measure the surrogate value, and determine the phase of the respiratory cycle as described previously with respect to step 100.

The new images are then used to update the three-dimensional CT images 16, 18 to which respiratory phase they correspond. In addition, the values of the surrogate signal are used to update the mean values (step 110). This may result in a slightly different relationship between the mean value of the surrogate signal and the most-likely position of the tumor, for example due to changes in average breathing pattern.

For example, the new images may be used to replace corresponding images obtained prior to treatment beginning, in step 100, i.e. "corresponding" in that they have similar gantry angles and breathing phase. Thus the surrogate-target relationship is updated based on a combination of new images and possibly old images, if a corresponding image has not been acquired in the later images.

As new images are acquired, new three-dimensional CT images are formed, and the surrogate-target position relationship is updated based on these images. This updated relationship between mean surrogate value and tumor location is used to treat the patient in real time, i.e. in the same treatment session (step 112). In step 113, it is determined whether the treatment should have finished, i.e. whether the predetermined treatment time has elapsed. If so, the treatment ends (step 114) and the linear accelerator is deactivated. If the treatment has not yet reached its conclusion, the process loops back to step 109, and continues to acquire new images, update the surrogate-target relationship, and continue treatment on the basis of the updated relationship. The present invention therefore provides a method of training a radiotherapy device to track and target a particular region (e.g. a tumor) of a patient on the basis of an easily measurable surrogate signal. The relationship between surrogate signal and tumor location is established prior to treatment beginning, and then continuously updated during the treatment by continuously imaging the target region of the patient, measuring the surrogate signal and determining the phase of the respiratory cycle.

Generally, the internal imaging of the patient can be carried out via cone-beam computed tomography ("CBCT"), as described above. However, other imaging modalities can be employed as desired.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A method of treating a cyclically varying target region in a patient, the method comprising:
   acquiring a first plurality of projection images of the patient interior;
   acquiring a signal from the patient, the signal being one capable of acting as a surrogate for a location of the target region in the patient;
   using the first plurality of projection images, establishing a relationship between location of the target region and the surrogate signal by the substeps of
      reconstructing a plurality of volumetric images of the patient from the first plurality of projection images, each volumetric image being reconstructed from projection images having a like breathing phase;
      identifying a position of the target region in each volumetric image;
      associating the surrogate signal with the projection images; and
      determining a relationship between the surrogate signal and the position of the target region in the volumetric images;
   beginning treatment of the target region on the basis of the surrogate signal and the established relationship;
      during said treatment, acquiring a second plurality of internal projection images of the patient,
      and updating the volumetric images using the second plurality of projection, images and updating the relationship on the basis the updated volumetric images; and
   continuing said treatment on the basis of the surrogate signal and said updated relationship.

2. A method according to claim 1 in which the first projection images are analysed for their breathing phase on the basis of a feature in the images, prior to reconstruction.

3. A method according to claim 1 in which the first projection images having a like breathing phase are grouped for reconstruction.

4. A method according to claim 1 in which multiple values of the surrogate signal associated with multiple projection images of the first plurality of projection images having a like breathing phase are used to determine a mean value of the surrogate signal for the location of the target region associated with that phase.

5. A method as claimed in claim 4, wherein said updating of the relationship comprises using values of the surrogate signal associated with images of said second plurality of projection images having said phase to update said mean value.

6. A method according to claim 1 in which multiple values of the surrogate signal associated with a like breathing phase are used to determine a variation of the value of the surrogate signal for the location of the target region associated with that phase.

7. A method according to claim 1, in which said treatment comprises directing a radiation beam towards said target region.

8. A radiotherapy apparatus, comprising:
a patient imaging system for obtaining internal imaging data of a patient, the system comprising a source of diagnostic x-radiation, and a detector therefor, and the internal images of the patient being, projection images obtained from the detector;
a sensor for obtaining a surrogate signal indicative of location of a target region in the patient;
a source of penetrating radiation for therapeutic purposes; and
control circuitry for directing a therapeutic beam of penetrating radiation towards the target region on the basis of imaging data provided by the patient imaging system;
the control circuitry being configured to:
receive a first set of imaging data;
receive surrogate signal values for the first set of imaging data;
establish a relationship between the location of the target region and the surrogate signal;
reconstruct a plurality of volumetric images of the patient from a first plurality of projection images, each volumetric image being reconstructed from projection images having a like breathing phase;
identify a position of the target region in each volumetric image;
associate the surrogate signal with the projection images;
determine a relationship between the surrogate signal and the position of the target region in the volumetric images;
begin treatment of the target region on the basis of the surrogate signal and the established relationship;
during said treatment, receive a second set of imaging data, update the volumetric images using a second plurality of projection images and update the relationship on the basis of the updated volumetric images; and
continue said treatment on the basis of the surrogate signal and the updated relationship.

9. An apparatus according to claim 8 in which the control circuitry is configured to analyse the projection images for their breathing phase on the basis of a feature in the images.

10. An apparatus according to claim 8 in which the control circuitry is configured to group projection images having a like breathing phase for reconstruction.

11. An apparatus according to claim 8 in which the control circuitry is configured to use multiple values of the surrogate signal associated with multiple patient images having a like breathing phase to determine a mean value of the surrogate signal for the location of the target region associated with that phase.

12. An apparatus as claimed in claim 11, wherein the control circuitry is configured to use values of the surrogate signal associated with images of the second plurality of projection images having said phase to update said mean value.

* * * * *

UNITED STATES PATENT AND TRADEMARK OFFICE
CERTIFICATE OF CORRECTION

PATENT NO. : 8,358,738 B2
APPLICATION NO. : 12/870256
DATED : January 22, 2013
INVENTOR(S) : Kevin Brown It is certified that error appears in the above-identified patent and that said Letters Patent is hereby corrected as shown below:

In the Claims

Claim 1, Column 6, Line 54-55: "internal" should be deleted
Claim 8 (original claim 10), Column 7, Line 25-26: "indicative of location" should be "indicative of a location"

Signed and Sealed this
Eighteenth Day of June, 2013

Teresa Stanek Rea
*Acting Director of the United States Patent and Trademark Office*